United States Patent [19]

Dessau

[11] 4,324,940

[45] Apr. 13, 1982

[54] SHAPE SELECTIVE ACID CATALYZED REACTIONS OF OLEFINS OVER CRYSTALLINE ZEOLITES

[75] Inventor: Ralph M. Dessau, Edison, N.J.

[73] Assignee: Mobil Oil Corporation, New York, N.Y.

[21] Appl. No.: 138,638

[22] Filed: Apr. 9, 1980

[51] Int. Cl.$^3$ .............................................. C07C 5/23
[52] U.S. Cl. ................................. 585/466; 208/111; 208/120; 260/340.7; 570/248; 585/407; 585/467; 585/533; 585/722
[58] Field of Search ......................................... 585/666

[56] References Cited

U.S. PATENT DOCUMENTS

| | | | |
|---|---|---|---|
| 3,150,202 | 9/1964 | Holt et al. | 260/683.2 |
| 3,791,964 | 2/1974 | Kuehl | 208/120 |
| 3,804,746 | 4/1974 | Chu | 585/666 |
| 4,108,881 | 8/1978 | Rollmann et al. | 423/328 |
| 4,146,584 | 3/1979 | Rollmann | 585/527 |

*Primary Examiner*—Curtis R. Davis

*Attorney, Agent, or Firm*—Charles A. Huggett; Michael G. Gilman; Dennis P. Santini

[57] ABSTRACT

Processes are provided for conducting selective acid catalyzed reactions involving olefins. Said catalytic reactions comprise isomerization, alkylation, addition, oligomerization, polymerization, aromatization, cracking and hydrocracking. The useful catalysts of this invention are the acidic forms of a novel class of zeolites characterized by a silica to alumina mole ratio of at least 12 and a constraint index in the approximate range of greater than about 2 to about 12. By utilization of such zeolites, smaller olefins are preferentially reacted when in mixed streams with larger olefins. Further of the such smaller olefins, linear olefins are preferentially reacted when in mixed streams with non-linear olefins and lesser branched olefins are preferentially reacted when in mixed streams with more highly branched olefins. Over the novel catalysts of this invention, para-disubstituted and/or mono-substituted aromatic olefins will react preferentially over ortho- and/or meta-disubstituted or more highly substituted aromatic olefins.

17 Claims, No Drawings

SHAPE SELECTIVE ACID CATALYZED REACTIONS OF OLEFINS OVER CRYSTALLINE ZEOLITES

BACKGROUND OF THE INVENTION

1. Field of the Invention

This invention relates to reactions of olefins catalyzed by shape selective acidic crystalline zeolites.

2. Description of the Prior Art

Acid catalyzed reactions of olefins comprise isomerization; alkylation; addition reactions, e.g. hydrogen halide addition, hydration, alcohol addition and the Prins reaction; dimerization; oligomerization; and polymerization; aromatization; cracking and hydrocracking.

Alkylation of aromatic hydrocarbons with an olefin in the presence of a crystalline metallic aluminosilicate having uniform pore openings of about 6 to 15 Angstom units is described in U.S. Pat. No. 2,290,607. U.S. Pat. No. 3,251,897 describes alkylation of aromatic hydrocarbons in the presence of X- or Y-type crystalline aluminosilicate zeolites, specifically such type zeolites wherein the cation is rare earth and/or hydrogen. U.S. Pat Nos. 3,751,504 and 3,751,506 describe vapor phase alkylation of aromatic hydrocarbons with olefins, e.g. benzene with ethylene, in the presence of a ZSM-5 type zeolite catalyst.

Also, U.S. Pat. No. 2,904,607 shows alkylation in the presence of certain crystalline zeolites. These zeolites, described for use in said patent, are crystalline metallic zeolites.

U.S. Pat. Nos. 3,631,120 and 3,641,177 describe a liquid phase process for the alkylation of aromatic hydrocarbons with olefins in the presence of certain zeolites.

Polymerization of olefins over HZSM-38 is disclosed in U.S. Pat. No. 4,046,859.

A process for producing Prins-type condensation products (addition reaction) is described in U.S. Pat. No. 3,414,588. The catalyst employed in this reaction of an aldehyde and an olefin is a faujasite-type zeolite.

Processes for the aromatization of olefins are described in U.S. Pat. Nos. 3,760,024 and 3,960,978. These processes utilize a ZSM-5 type acidic zeolite catalyst.

It has long been known to contact various hydrocarbon fractions with acidic catalysts and, in particular, with solid siliceous acidic catalysts - including those referred to as crystalline zeolites. Contact of said hydrocarbon feed with said acid catalysts was carried out for a wide variety of reactions including cracking, isomerization, hydrocracking, etc. Representative U.S. patents disclosing and claiming the contacting of various hydrocarbon fractions with crystalline zeolites are U.S. Pat. Nos. 3,140,249; 3,140,251; 3,140,253 and 3,140,322.

The use of acid Mordenite for cracking, alkylation, isomerization and olefin polymerization is disclosed in U.S. Pat. No. 3,597,493.

U.S. Pat. No. 3,758,602 describes a process for selectively cracking polar compounds from non-polar saturated hydrocarbons in the presence of a crystalline aluminosilicate catalyst.

SUMMARY OF THE INVENTION

In accordance with the present invention, there has now been discovered processes for conducting acid catalyzed reactions of olefins. Smaller olefins, as defined as having "effective critical dimensions" of 6.8 Angstroms, as measured on molecular models, and less, will react in the presence of the acid zeolite catalysts of this invention, while larger olefins, i.e. having "effective critical dimensions" in excess of 6.8 Angstroms will not react. Further, of these "smaller olefins", linear olefins will react preferentially over the novel acid zeolite catalysts of the instant invention as they occur in mixed streams with branched-chain (nonlinear) olefins. Also lesser branched-chain olefins of the class of smaller olefins will react preferentially as they occur in mixed streams with greater branched isomers over the acid zeolite catalysts of this invention. Also of this class of "smaller olefins", para-disubstituted aromatic olefins and/or mono-substituted aromatic olefins will react preferentially over ortho- and/or meta disubstituted or more highly substituted aromatic olefins when contacted with the novel acid zeolite catalysts of the present invention.

The presence of the novel zeolite catalysts of the instant invention are such that they change the relative acid catalyzed reactivities of olefins from that observed over conventional acid catalysts, e.g. other zeolites, silica-alumina, hydrofluoric acid, sulfuric acid, etc. In some of the processes embraced by this invention, the order of acid catalyzed activity is unexpectly, completely reversed. For example, whereas branched-chain olefins are more reactive over linear olefins when contacted by the aforesaid conventional acid catalysts, using the novel acid zeolite catalysts of the present invention results in linear olefins reacting in preference to branched olefins. Similarly, in accordance with this invention, lesser branched olefins react preferentially over greater branched olefins when in contact with the novel acid zeolite catalysts of this invention.

The catalysts utilized in this invention comprise acidic crystalline zeolites and acidic crystalline zeolites modified to increase their shape selective potential. Said zeolites are characterized by a silica to alumina mole ratio of at least 12 and a constraint index, as hereinafter defined, within the approximate range of greater than about 2 to about 12.

DESCRIPTION OF THE PREFERRED EMBODIMENTS

The instant invention is accomplished by contacting a mixed stream of olefins over the acidic crystalline zeolites of this invention in order to carry out acid catalyzed reactions of olefins.

In one aspect of this invention, smaller olefins with "effective critical dimensions" of 6.8 Angstroms, as measured on molecular models, and less will react when contacted with the novel zeolite acid catalysts of this invention, while larger olefins will not react, i.e. olefins with effective critical dimensions of greater than 6.8 Angstroms.

The "effective critical dimension" of a molecule is described by Breck on pages 633 to 641 in *Zeolite Molecular Sieves*, John Wiley & Sons, Inc. (1974), the entire contents of which are incorporated herein by reference. Generally, this dimension is the smallest dimension that will permit passage through the pores of the zeolite, i.e. the dimension that most nearly approaches the pore size of the zeolite. For example, the critical dimension of n-hexane is the thickness not the length, while the critical dimension for benzene is the cross-sectional diameter, rather than the thickness.

Various olefins may be employed in the processes of this invention. These olefins may be monoolefins or diolefins and may be acyclic monoolefins or diolefins and cyclic monoolefins or diolefins. The diolefins may be conjugated or non-conjugated. The acyclic monoolefins may be straight chain or branched chain monoolefins and may contain between 2 to 200 carbon atoms. Preferably, however, the acyclic monoolefins contain between 2 and 92 carbon atoms and, still more preferably, contain between 2 and 10 carbon atoms. The acyclic diolefins may contain between 3 and 8 carbon atoms. The cyclic monoolefins may contain between 5 and 8 carbon atoms and the cyclic diolefins may also contain between 5 and 8 carbon atoms. The acyclic monoolefins may contain one or more aromatic groups, preferably phenyl groups. Further, the acyclic monoolefins may contain chlorine or bromine substitutents or a carboxy or carboxymethyl substituent.

Suitable illustrative olefins include ethylene, propylene, the butenes, pentenes, hexenes, heptenes, octenes, monenes, and decenes. Other acyclic monoolefins which may be employed are olefin oligomers such as propylene and isobutylene tetramer, isobutylene trimer, and propylene pentamer and hexamer. Other suitable illustrative olefins include allene, butadiene, pentadiene, isoprene, biallyl, heptadiene, and bimethallyl. Still other suitable illustrative olefins include cyclopentene, cyclohexene, cycloheptene, cyclooctene, cyclopentadiene, cyclohexadiene, cycloheptadiene, and cyclooctadiene. Acyclic monoolefins containing one or more aromatic groups include styrene, methyl styrene, stilbene, 1,1-diphenyl ethylene, and methyl cinnamate. Representative olefins containing chlorine, bromine, carboxy or carboxymethyl substituents include bromostyrene, methyl cinnamate, methylacrylate, dimethyl maleate, polychloroethylene, oleic acid and methyl oleate.

It will be seen that the foregoing olefins are those of the formula

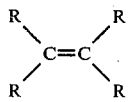

wherein one or more of the R's are hydrogen, straight or branched chain alkyl, aryl, alkaryl or aralkyl groups, the total number of carbon atoms in the alkyl groups being between 1 and 198, an alkenyl group containing 1 to 100 carbon atoms. Each of these above constituent groups may contain one or more substitutents such as halogens, e.g. chlorine, bromine; carbonyl; carboxy; or carboxyalkyl. Also included are olefins where two R groups are connected to form a cyclic structure of total ring size ranging from 4 to 10.

Non-limiting examples of "Smaller Olefins" include all linear olefins, e.g. propylene, butylene, hexene, decene, etc; methyl branched olefins, such as isobutylene; dimethyl branched olefins; and some aromatic containing olefins, such as styrene and allylbenzene. Non-limiting examples of "larger olefins" include 1-allylnaphthalene, 3,5-dimethylstyrene and cyclooctene.

In another aspect of this invention, such "smaller olefins" are preferentially reacted when in mixed streams depending on branching and aromatic substitution, e.g. para, ortho or meta, etc. Linear olefins will preferentially react when in mixed streams with non-linear olefins over the novel acidic zeolite catalysts of this invention. Non-limiting examples of such linear olefins include ethylene, propylene, pentene, heptene, nonene, etc. Non-limiting examples of branched olefins include 2-methylpropene; 3,3-dimethyl-1-butene, 4-methyl-2-pentene, etc. Similarly, lesser branched olefins such as mono-alkyl olefins will react preferentially over greater branched olefins such as di-or polyalkyl substituted olefin when in contact with the novel acidic zeolite catalysts of the instant invention. For example, 2-methylpropene will react preferentially over 3,3-dimethyl-1-butene. Further, a monomethyl substituted olefin will be preferentially react relative to an ethyl or larger substituted olefin.

In a further aspect of the present invention dealing with such "smaller olefins", para-disubstituted aromatic olefins or mono-substituted aromatic olefins are preferentially reacted when in mixed streams with ortho- or meta- disubstituted or more highly substituted aromatic olefins when contacted with the novel acidic zeolite catalysts of the instant invention. Non-limiting examples of such selective acid catalyzed reactions include the selective reaction of para-methylstyrene in mixed stream with ortho-methylstyrene and the selective reaction of para-allyltoluene in mixed stream with meta-allyltoluene.

All acid catalyzed reactions of olefins such as isomerization, alkylation, addition, dimerization, oligomerization, polymerization, aromatization, cracking, and hydrocracking, etc., would be shape selective over the novel class of crystalline zeolites of this invention.

The selective acid catalyzed reactions of this invention can also be utilized to selectively remove small amounts of the reactive olefins from the less reactive olefins. For example, para divinyl benzene can be removed from ortho divinyl benzene by selective reaction of the para compounds.

Isomerization reactions include both the alteration of the arrangement of atoms in a molecule without changing the total number of atoms, i.e. skeletal atom isomerization, or the rearrangement of multiple bond, i.e. double bond isomerization. Conversion conditions for isomerization include a temperature of between about 450° F. and about 1000° F., a pressure of between about 0 and about 500 psig, a WHSV of between about 0.1 and 200 hr$^{-1}$, and a hydrogen to olefin mole ratio of between about 0.1 and about 100.

The addition of an alkene (olefin) and an alkane (paraffin) over an acid is one example of an alkylation reaction. This reaction is represented by the following general formula:

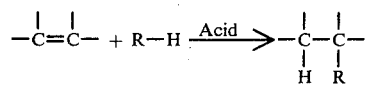

An important alkylation reaction of this type is the addition of isobutylene and isobutane in the presence of acid catalysts to form 2,2,4-trimethylpentane, an aviation fuel. Alkylations can also involve the addition of olefins and aromatic hydrocarbons. Typical of such aromatic alkylation is the combination of ethylene and benzene to form ethylbenzenes. Alkylation can be generally defined as the union of an unsaturated and a saturated compound to form a saturated, branched chemical compound. Conditions for conducting alkylations include a temperature of between about 100° F. and 950° F., a pressure of between about atmospheric and 900 psig and a WHSV of between about 1 and 500.

Hydration is the addition of water to an olefin to form an alcohol in the presence of an acid catalyst. This reaction is represented by the following general formula:

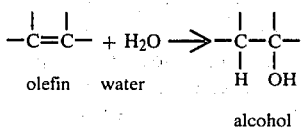

olefin   water        alcohol

Hydration reactions can be conducted at temperatures in the approximate range of between about 150° F. and 600° F. and at pressures of between atmospheric and about 100 atmospheres.

Hydrogen halide addition is the reaction of an olefin and a member of the group consisting of HCl, HBr and HI. A typical reaction of this kind is represented by the following general equation:

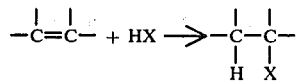

where X = Cl, Br, or I

Addition reactions of this nature can be conducted at temperature below about 800° F. and at pressures ranging between atmospheric and up to 100 atmospheres.

Another addition reaction is the Prins reaction. Prins-type products include alcohols, glycols, diolefins, alkyl m-dioxanes, and the like. In a typical Prins reaction, an aldehyde is reacted with an olefin in the presence of an acid catalyst. For example, the reaction of formaldehyde and isobutylene will produce a product mixture of 4,4-dimethyl-m-dioxane and 3-methyl-1,3-butanediol. The Prins reaction can be conducted at temperatures ranging from room temperature up to about 800° F.

Also included in the class of acid catalyzed addition reactions is alcohol addition to olefins to form ethers. Conditions for conducting such alcohol addition are similar to those described above for hydration.

Dimerization involves the addition of alkenes (olefins) in the presence of an acid catalyst. Dimerization conditions include a temperature of between about 0° F. and 1200° F., a pressure of between about atmospheric and 100 atmospheres, preferably between about atmospheric and 25 atmospheres and a WHSV of between about 0.1 and 30 hr$^{-1}$, preferbly between about 0.5 and 10. A typical dimerization reaction involves the addition of two propylene molecules to form dimethylbutenes.

Oligomerization and polymerization involve the linking of similar molecules in the presence of heat and a catalyst to form bigger molecules. Oligomerization involves the forming of dimers, trimers and quatramers, whereas a typical polymerization concerns the joining of light olefins to form a very long chain olefin. Olefin oligomerization and polymerization conditions include a temperature of from about 95° to about 935° F., preferably from about 390° F. to about 810° F., a pressure of from about atmospheric to about 10,000 psig, preferably from about atmospheric about 2,000 psig, a WHSV (when a flow operation) of from about 0.1 hr$^{-1}$ to about 50 hr$^{-1}$, preferably from about 0.5 hr$^{-1}$ to about 10 hr$^{-1}$, and a contact time (when a batch operation) of from about 0.1 hour to about 48 hours, preferably from about 0.5 hour to about 24 hours and a hydrogen/olefin mole ratio of from about 0 to about 20, preferably from about 0 to about 10.

The formation of aromatic compounds by reacting paraffins, olefins and mixtures thereof over acids is defined as aromatization. A typical aromatization is the reaction of a feed stream containing essentially $C_2$-$C_4$ paraffins (ethane, propane, butane, isobutane) and/or olefins (ethylene, propylene, butene, isobutene), and mixtures thereof with an acidic catalyst to produce predominantly $C_6$-$C_{10}$ aromatics.

When the acid catalyzed reaction is aromatization, catalytic conversion conditions should be maintained within certain ranges, including a temperature of from about 550° F. to about 1200° F., preferably from about 650° F. to about 1100° F., a pressure of from about atmospheric to about 10,000 psig, preferably from about atmospheric to about 2000 psig, a WHSV (when a flow operation) of from about 0.1 hr$^{-1}$ to about 10 hr$^{-1}$, preferably from about 1 hr$^{-1}$ to about 5 hr$^{-1}$, a contact time (when a batch operation) of from about 0.1 hour to about 48 hours, preferably from about 1 hour to about 24 hours and a hydrogen/olefin mole ratio of from about 0 to about 20, preferably from about 0 to about 10.

Further, when the acid catalyzed reaction by the present process is cracking, catalytic conversion conditions should be maintained within certain ranges, including a temperature of from about 700° to about 1200° F., preferably from about 800° to about 1100° F., a pressure of from about atmospheric to about 200 psig, a WHSV (when a flow operation) of from about 0.5 hr$^{-1}$ to about 50 hr$^{-1}$, preferably from about 1 hr$^{-1}$ to about 10 hr$^{-1}$, and a contact time (when a batch operation) of from about 0.01 hour to about 24 hours, preferably from about 0.1 hour to about 10 hours.

When the reaction is hydrocracking, catalytic conversion conditions should be maintained within somewhat different ranges, including a temperature of from about 400° to about 1000° F., preferably from about 500° to about 850° F., a pressure of from about 500 psig to about 3500 psig, a WHSV (when a flow operation) of from about 0.1 hr$^{-1}$ to about 10 hr$^{-1}$, preferably from about 0.2 hr$^{-1}$ to about 5 hr$^{-1}$, a contact time (when a batch operation) of from about 0.1 hour to about 10 hours, preferably from about 0.2 hour to about 5 hours and a hydrogen/olefin mole ratio of from about 1 to about 20, preferably from about 3 to about 10. The hydrocracking catalyst may contain a metal function such as platinum, nickel and palladium.

The novel class of crystalline zeolites of this invention is characterized by a constraint index, as hereinafter defined, in the approximate range of greater than about 2 to about 12 and a silica to alumina ratio of at least 12.

In reactions dealing with the "smaller olefins", selectively for the preferred olefins can be increased by effecting various modifications to the useful zeolites of this invention. Such modifications include partial ion exchange with bulky cations, the use of larger crystal sizes for the useful zeolites, and coke selectivation of the useful zeolites. To increase selectivity, bulky cations such as the heavy metals of Group IA of the Periodic Table of Elements, e.g., Rb, Cs, and tetramethylammonium (TMA) can be exchanged onto the useful zeolites of this invention.

Another method to increase selectivity is to utilize larger crystal sizes for the useful zeolites of this invention. Thus use of a zeolite with a crystal size of 0.5 to 100 microns and larger (hereinafter referred to as larger crystal size zeolite) will be more selective than the same zeolite with a crystal size of about 0.02 to 0.5 microns (hereinafter referred to as small crystal size zeolite).

Still another method to increase selectivity is coke selectivation. Coke selectivation involves depositing an amount of carbon on the useful zeolite of this invention to improve its selectivity.

The zeolite catalysts herein described are members of a novel class of zeolites exhibiting some unusual properties. These catalysts induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina mole ratios, they are very active even when the silica to alumina mole ratio exceeds 30. The activity is surprising, since catalytic activity for such transformations is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments, the zeolites of this class exhibit very low coke forming capability, conducive to very long times on stream between burning regenerations.

An important characteristic of the crystal structure of this class of zeolites is that it provides constrained access to, and egress from, the intracrystalline free space by virtue and having a pore dimension greater than about 5 Angstroms and pore windows of about a size such as would be provided by 10-membered rings of silicon atoms interconnected by oxygen atoms. It is to be understood, of course, that these rings are those formed by the regular disposition of the tetrahedra making up the anionic framework of the crystalline zeolite the oxygen atoms themselves being bonded to the silicon or aluminum atoms at the centers of the tetrahedra. Briefly, the preferred type catalyst useful in this invention possesses, in combination: a silica to alumina mole ratio of at least about 12 and a structure providing constrained access to the crystalline free space.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina mole ratio of at least 12 are useful, it is preferred to use catalysts having higher ratios of at least about 30. Such catalysts, after activation, acquire an intracrystalline sorption capacity for normal hexane which is greater than that for water, i.e. they exhibit "hydrophobic" properties.

The zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous selectivities, although puckered structures exist such as TMA offretite which is a known effective zeolite. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of a equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly space velocity (i.e. 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\text{Log}_{10} \text{ (fraction of n-hexane remaining)}}{\text{Log}_{10} \text{ (fraction of 3-methylpentane remaining)}}$$

The Constraint Index approximates the ratio of the cracking rate constants for the two hydrocarbons. Zeolites suitable for the present invention are those having a constraint index in the approximate range of greater than 2 to about 12. Constraint Index (C.I.) values for some typical catalysts are:

| ZEOLITE | C.I. |
|---|---|
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |
| Clinoptilolite | 3.4 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indices. Constraint Index seems to vary somewhat with severity of operation (conversion) and the presence or absence of binders. Therefore, it will be appreciated that it may be possible to so select test conditions to establish more than one value in the range of greater than about 2 to about 12 for the Constraint Index of a particular zeolite. Such a zeolite exhibits the constrained access as herein defined and is to be regarded as having a Constraint Index of greater than about 2 to about 12. Also contemplated herein as having a Constraint Index of greater than about 2 to about 12 are those zeolites which, when tested under two or more sets of conditions within the above specified ranges of temperature and conversion, produce a value of the Constraint Index slightly less than 2, e.g. 1.9, or somewhat greater than 12, e.g. 14 or 15, with at least one other value of greater than about 2 to about 12. Thus, it should be understood that the Constraint Index value as used herein in an inclusive rather than an exclusive value. That is, a zeolite when tested by any combination of conditions within the testing definition set forth hereinabove to have a Constraint Index of greater than about 2 to about 12 is intended to be included in the instant catalyst definition regardless that the same identical zeolite tested under other defined conditions may give a Constraint Index value outside of greater than about 2 to about 12.

The class of zeolites defined herein is exemplified by ZSM-5, ZSM-11, ZSM-23, ZSM-35, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F. for 1 hour, for example, followed by base exchange with ammonium salts, followed by calcination at 1000° F. in air. The presence of organic cations in the forming solution may not be absolutely essential to the formation of this type of zeolite; however, the presence of these cations does appear to favor the formation of this special type of zeolite. More generally, it is desirable to activate this type catalyst by base exchange with ammonium salts, followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of greater than about 2 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper is included in "Proceedings of the Conference on Molecular Sieves, London, April, 1967", published by the Society of Chemical Industry, London, 1968. When the crystal structure is unknown, the crystal framework density may be determined by classical pycnometer techniques. For example, it may be determined by immersing the dry hydrogen form of the zeolite in an organic solvent which is not sorbed by the crystal. It is possible that the unusual sustained activity and stability of this class of zeolites are associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolites | Void Volume | Framework Density |
| --- | --- | --- |
| Ferrierite | 0.28 cc/cc | 1.76 g/cc |
| Mordenite | .28 | 1.7 |
| ZSM-5,11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.2 |
| Y | .48 | 1.27 |

When synthesized in the alkali metal form, the zeolite is conveniently converted to the hydrogen form, generally by intermediate formation of the ammonium form as a result of ammonium ion exchange and calcination of ammonium form to yield the hydrogen form. In addition to the hydrogen form, other forms of the zeolite wherein the original alkali metal has been reduced to less than about 1.5 percent by weight may be used. Thus, the original alkali metal of the zeolite or introduced hydrogen cations may be replaced by ion exchange with other suitable ions of Groups IB to VIII of the Periodic Table, including, by way of example, nickel, cadmium, copper, zinc, palladium, calcium or rare earth metals.

In practicing the desired synthesis method, it may be desirable to incorporate the above-described crystalline zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occuring clays, which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in a raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The following Examples will serve to illustrate the process of the invention without limiting same.

EXAMPLE 1

This example illustrates the preparation of smaller crystal size ZSM-5 zeolite.

An organics salt solution, was prepared by mixing 1.6 parts of n-propyl bromide, 1.9 parts of tri-n-propylamine, 3.1 parts of methyl ethyl ketone and 10.4 parts of water. The mixture was reacted at about 100° C. for about 14 hours. The aqueous phase of the reacted mixture is designated Solution A.

A sodium silicate solution was prepared by mixing 16 parts water and 27.7 parts sodium silicate (28.7 wt. %) $SiO_2$, 8.9 wt. % $Na_2O$, 62.4% $H_2O$) followed by addition of 0.08 parts Daxad 27 (W. R. Grace Chem. Div.). The solution was cooled to approximately 15° C.

An acid solution was prepared by adding 1 part aluminum sulfate (17.2 wt. % $Al_2O_3$) to 16.4 parts water followed by 2.4 parts NaCl and 2.9 parts of Solution A.

These solutions were mixed in an agitated vessel while 3.9 parts of NaCl were added. The gel molar ratios expressed as oxides are the following.

$SiO_2/Al_2O_3 = 78.4$
$Na_2O/Al_2O_3 = 49.9$

The gel was agitated for 4 hours at ambient temperature then heated to 95°–110° C. and held for 40 hours with severe agitation. When approximately 65% of the gel was crystallized, the temperature was increased to 150°–160° C. and held there until crystallization was complete.

The zeolite slurry product was diluted with 4–5 parts water per part slurry and 0.002 parts of flocculent (Rohm & Hass Primafloc C-7) per part slurry, allowed to settle and supernatant liquid was drawn off. The settled solids were reslurried to the original volume of the preceding step with water and 0.00005 parts of flocculent per part slurry. After settling, the aqueous phase was decanted. This procedure was repeated until the sodium level of the zeolite was less than 1.0 wt. %. The washed zeolite was then filtered, dried and identified as ZSM-5 having a silica/alumina mole ratio of at least 12; i.e., about 70, and a constraint index of between 1 and 12; i.e., about 8.3.

The dried zeolite product was calcined in flowing $N_2$ for 3 hours at 538° C. than ion exchanged twice with 1 N $NH_4NO_3$ solution (5 parts $NH_4NO_3$ solution/1 part zeolite) for 1 hour at ambient temperature and dried at about 120° C.

EXAMPLE 2

This example illustrates the preparation of larger crystal size ZSM-5 zeolite.

A sodium silicate solution was prepared by mixing 16 parts water and 27.7 parts sodium silicate (28.7 wt. % $SiO_2$, 8.9 wt. % $Na_2O$, 62.4% $H_2O$) followed by addition of 0.08 parts Daxad 27 (W. R. Grace Chem. Co.) The solution was cooled to approximately 15° C.

An acid solution was prepared by adding 1 part aluminum sulfate (17.2 wt. % $Al_2O_3$) to 16.4 parts water followed by 2.4 parts sulfuric acid (93 wt. % $H_2SO_4$) and 1.2 parts NaCl.

These solutions were mixed in an agitated vessel while 3.9 parts of NaCl were added. The gel molar ratios expressed as oxides are the following:

$SiO_2/Al_2O_3 = 78.4$
$Na_2O/Al_2O_3 = 49.9$

An organic solution was prepared by adding 1.6 parts n-propyl bromide and 3.1 parts methyl ethyl ketone to 1.9 parts tri-n-propylamine and added to the gel.

The mixture was reacted at 150°–160° F. with severe agitation for 29 hours.

The zeolite slurry product was diluted with 4–5 parts water per part slurry and 0.0002 parts of flocculent (Rohm & Haas Primafloc C-7) per part slurry, allowed to settle and supernatant liquid was drawn off. The settled solids were reslurried to the original volume of the preceding step with water and 0.00005 parts of flocculent per part slurry. After settling, the aqueous phase was decanted. This procedure was repeated until the decant supernatant liquid was Cl- free. The washed zeolite was then filtered, dried and identified as ZSM-5 having a silica/alumina mole ratio of at least 12; i.e., about 70, and a constraint index of between 1 and 12; i.e., about 8.3.

The dried zeolite product was calcined in flowing $N_2$ for 3 hours at 538° C. then ion exchanged twice with 1 N $NH_4NO_3$ solution (5 parts $NH_4NO_3$ soln/1 part zeolite) for 1 hour at ambient temp. and dried at about 120° C.

EXAMPLE 3

Cs-H-ZSM-5 was made by exchanging $NH_4$-ZSM-5 from Example 1 (10 g) with 220 cc of a 0.1 M CsCl solution overnight. Ammonia analysis indicated 98.7% exchange took place.

EXAMPLE 4

TMA-H-ZSM-5 was made by exchanging 26 g $NH_4$-ZSM-5 from Example 1 with 700 ml 1 M tetramethylammonium bromide containing sufficient TMA hydroxide to raise the ph above 11. The catalyst prior to use was heated in a fixed bed glass reactor under flowing nitrogen at 390° C. to 400° C. for exactly 6 minutes, so that only a portion of the TMA ions would decompose to generate acidic sites.

All the olefins used in the foregoing examples were obtained in 99+% purity from Chemical Samples Company.

EXAMPLES 5 TO 10

Examples 5 to 10 illustrate competitive isomerization reactions of olefins conducted over acidic ZSM-5 catalysts at temperatures in the range of 100° C. to 175° C. Results of these examples are given in Table 1.

The catalysts of Examples 5 to 7 were prepared by the general procedure of Example 1. The catalysts of Examples 8 to 10 were prepared by the general procedure of Example 2.

The competitive isomerization reactions were run in a down-flow fixed bed glass reactor. An equimolar solution of the two olefins were fed into the reactor by means of a syringe pump and diluted with a flow of nitrogen. The product mixture was analyzed by means of an on-line gas chromatograph containing a 10 ft. n-octane-Durapak column.

The relative diffusivities of variously shaped olefins in ZSM-5 were obtained from competitive isomerization reactions conducted over H-ZSM-5 at temperatures in the 100° C. to 175° C. range (see Table 1). Both single- and double-branched molecules were studied, and in all cases the shape selectivities were somewhat greater for the larger crystal size zeolite.

Shape selectivity was observed as follows:
linear olefin > methyl-branched >>
ethyl-branched > gem-dimethyl-branched

TABLE 1

| Ex. No. | Catalyst | Temperature °C. | Competitive Isomerizations A | B | % Conversion A | % Conversion B | Selectivity kA/kB |
|---|---|---|---|---|---|---|---|
| 5 | (b)H—ZSM—5 | 105 | hexene-1 | 6-Me heptene-1 | 59 | 47 | 1.4 |
| 6 | (b)H—ZSM—5 | 125 | hexene-1 | 3-Et pentene-1 | 64 | 10 | 9.7 |
| 7 | (b)H—ZSM—5 | 100 | hexene-1 | 4,4-diMe hexene-1 | 47 | 2.6 | 25 |
| 8 | (a)H—ZSM—5 | 150 | hexene-1 | 6-Me heptene-1 | 41 | 25 | 1.8 |
| 9 | (a)H—ZSM—5 | 175 | hexene-1 | 3-Et pentene-1 | 64 | 2.8 | 35 |
| 10 | (a)H—ZSM—5 | 175 | hexene-1 | 4,4-diMe hexene-1 | 54 | 0.65 | 120 |

(a)larger crystal size zeolites
(b)smaller crystal size zeolites

EXAMPLES 11 TO 13

The effect of cation exchange on selectivity is illustrated by Examples 11 to 13 and shown in Table 2. These examples are based on the competitive isomerization of hexene-1 and 6-Me heptene-1. Example 11 is the same as Example 5, and Examples 11 to 13 follow the general experimental procedure as used in Examples 5 to 10.

The catalyst for Example 11 was prepared according to the general procedure of Example 1. In Example 12, the catalyst used was prepared in accordance with the general procedure of Example 3, and in Example 13 the catalyst was prepared in accordance with the general procedure of Example 4.

The shape selectivity of acid catalyzed reactions of olefins over zeolites can be accentuated by the presence of large cations exchanged onto the zeolite. In particular, the preference for linear olefins was enhanced for both cesium and tetramethylammonium exchanged ZSM-5 as shown in Table 2.

TABLE 2

Effect of Cation Exchange on Selectivity

| Ex. No. | Catalyst | Temperature °C. | Selectivity (hexane-1 6-Me heptene-1) |
|---|---|---|---|
| 11 | (a)H—ZSM—5 | 105 | 1.4 |
| 12 | (a)Cs—H—ZSM—5 | 100 | 3.0 |
| 13 | (a)TMA—H—ZSM—5 | 100 | 3.3 |

(a)smaller crystal size zeolite

EXAMPLE 14

An equimolar sample of allylbenzene and 1-allyl-naphthalene was contacted with HZSM-5 as prepared according to Example 1, at 100° C. for 5 hours. Allylbenzene was extensively isomerized (double bond isomerization), while the 1-allyl-naphthalene was unreacted. This Example serves to illustrate the selective acid catalyzed reaction of a "smaller olefin" in admixture with a "larger olefin", i.e. 1-allyl-naphthalene with an effective critical dimension greater than 6.8 Angstroms.

EXAMPLE 15

A mixture of octene-1 and di-isobutylene is contacted in a down-flow fixed bed reactor with HZSM-5, as prepared according to Example 1, at 300° C., atmospheric pressure and at a WHSV of 10. The linear olefin, octene-1, is preferentially cracked to light gases, whereas the branched olefin, di-isobutylene remains largely intact.

EXAMPLE 16

A mixture of isobutylene and 2,4,4-trimethylpentene-1 is contacted in a down-flow fixed bed reactor with HZSM-5, as prepared according to Example 1, at conditions including a temperature of 300° C., atmospheric pressure and a WHSV of 10. The lesser branched olefin, isobutylene, is preferentially cracked to light gases, whereas the more highly branched olefin, 2,4,4-trimethylpentene-1, remains generally unreacted.

EXAMPLE 17

A mixture of alpha methyl styrene dimer and phenyl hexene is contacted in a down-flow fixed bed reactor with HZSM-5, as prepared according to Example 1, at conditions including a temperature of 300° C., a pressure of 1 atmosphere and a WHSV of 10. Phenyl hexene, a linear olefin, is preferentially cracked, while alpha methyl styrene dimer remains essentially unreacted.

EXAMPLE 18

A mixture of propylene, a linear olefin, and dimethyl-hexene, a branched olefin, is contacted in a batch reactor with HZSM-5, as prepared according to the general procedure of Example 1, at conditions including a temperature of 100° C., a pressure of 100 psig and a residence time of 1 hour. The resulting product is a mixture of $C_6$, $C_9$ and $C_{12}$ olefins thus indicating selective oligomerization of the propylene, rather than dimethylhexane.

EXAMPLE 19

Following the same procedure and reaction conditions of Example 18, styrene and 3,5-dimethylstyrene are passed over HZSM-5. The product of this competitive reaction indicates polymerization of styrene with 3,5-dimethylstyrene remaining almost unreacted.

EXAMPLE 20

A mixture of heptene-1 and 4,4-dimethylpentene-1 is contacted in a down-flow fixed bed reactor with HZSM-5, as prepared according to Example 1, at conditions including a temperature of 400° C., a pressure of 100 psig and a WHSV of 1. The product contains aromatics with a significant proportion of the 4,4-dimethylpentene-1 remaining unreacted.

EXAMPLE 21

This example illustrates a typical addition reaction conducted according to this invention. A mixture of hexene-1 and 3,3-dimethylbutene-1 is contacted in a down-flow fixed bed reactor with HZSM-5, as prepared according to Example 1. The reaction is conducted in the presence of steam at 150° F., 50 atmospheres pressure and a WHSV of 1. A mixture containing hexylalcohols is formed, while the 3,3-dimethylbutene-1 remains essentially unreacted.

EXAMPLE 22

A mixture of hexene-1 and dimethylbutene-1 is contacted in a down-flow fixed bed reactor with HZSM-5, as prepared according to Example 1. The reaction is conducted in the presence of benzene at 300° C., a WHSV of 10 and 100 psig. The products contain a mixture of hexylbenzenes, while the dimethylbutene-1 remains largely unreacted.

What is claimed is:

1. In a process for effecting reaction involving olefins in a stream containing olefins of various sizes which comprises contacting said stream at a temperature of from about 450° F. to about 1000° F., a pressure of from about 0 psig to about 500 psig, a weight hourly space velocity of from about 0.1 hr$^{-1}$ to about 200 hr$^{-1}$ and a hydrogen/olefin mole ratio of from about 0.1 to about 100 with a catalyst comprising one or more members of a class of crystalline zeolites characterized by a silica/alumina mole ratio of at least 12 and a Constraint Index within the approximate range of greater than about 2 to about 12, the improvement which comprises (1) said stream containing smaller olefins of an effective critical dimension of 6.8 Angstroms or less and larger olefins of an effective critical dimension of greater than 6.8 Angstroms and (2) said catalyst being acidic, whereby said reaction is preferentially selective toward said smaller olefins.

2. In a process for effecting reaction involving olefins in a stream containing olefins of various shapes which comprises contacting said stream at a temperature of from about 450° F. to about 1000° F., a pressure of from about 0 psig to about 500 psig, a weight hourly space velocity of from about 0.1 hr$^{-1}$ to about 200 hr$^{-1}$ and a hydrogen/olefin mole ratio of from about 0.1 to about 100 with a catalyst comprising one or more members of a class of crystalline zeolites characterized by a silica/alumina mole ratio of at least 12 and a Constraint Index within the approximate range of greater than about 2 to about 12, the improvement which comprises (1) said stream containing both linear and branched olefins having effective critical dimensions of 6.8 Angstroms or less and (2) said catalyst being acidic, whereby said reaction is preferentially selective toward said linear olefins.

3. The process of claim 1 wherein said reaction is isomerization.

4. The process of claim 2 wherein said reaction is isomerization.

5. The process of claim 1 or 2 wherein said one or more members of a class of crystalline zeolites has been ion-exchanged with hydrogen or a hydrogen precursor.

6. The process of claim 1 or 2 wherein said one or more members of a class of crystalline zeolites has been partially ion-exchanged with cations selected from the group consisting of rubidium, cesium and tetramethylammonium.

7. The process of claim 5 wherein said one or more members of a class of crystalline zeolites has been also partially ion-exchanged with cations selected from the group consisting of rubidium, cesium and tetramethylammonium.

8. The process of claim 1 or 2 wherein one or more members of said class of crystalline zeolites has a crystal size of from about 0.5 micron to larger than about 100 microns.

9. The process of claim 5 wherein one or more members of said class of crystalline zeolites has a crystal size of from about 0.5 micron to larger than about 100 microns.

10. The process of claim 1 or 2 wherein one or more of said class of crystalline zeolites has been deposited with coke.

11. The process of claim 5 wherein one or more of said class of crystalline zeolites has been deposited with coke.

12. The process of claim 1 or 2 wherein said crystalline zeolites are selected from the group consisting of ZSM-5, ZSM-11, ZSM-23 and ZSM-35.

13. The process of claim 5 wherein said crystalline zeolite is ZSM-5.

14. The process of claim 7 wherein said crystalline zeolite is ZSM-5.

15. The process of claim 12 wherein said crystalline zeolite is ZSM-5.

16. The process of claim 14 wherein the crystalline zeolite is Cs-H-ZSM-5.

17. The process of claim 14 wherein the crystalline zeolite is TMA-H-ZSM-5.

* * * * *